United States Patent [19]

Losch

[11] Patent Number: 4,800,877
[45] Date of Patent: Jan. 31, 1989

[54] LASER OUTPUT CALIBRATION TAB

[75] Inventor: Richard C. Losch, Union City, Calif.

[73] Assignee: Laserscope, Santa Clara, Calif.

[21] Appl. No.: 866,601

[22] Filed: May 23, 1986

[51] Int. Cl.$^4$ ............................................. A61B 17/36
[52] U.S. Cl. ................................................. 128/303.1
[58] Field of Search ............ 128/4, 6, 303.1, 395–398;
73/1 R; 219/121 LA, 121 LB, 121 LZ; 362/32;
350/96.15, 96.16, 96.20, 96.23; 372/20, 29–32;
374/32

[56] References Cited

U.S. PATENT DOCUMENTS

| | | | |
|---|---|---|---|
| 3,487,835 | 1/1970 | Koester et al. | 128/303.1 |
| 3,721,815 | 3/1973 | Wall | 362/32 |
| 3,865,113 | 2/1975 | Sharon et al. | 128/303.1 |
| 4,091,814 | 5/1978 | Togo | 128/303.1 |
| 4,122,853 | 10/1978 | Smith | 128/303.1 |
| 4,215,694 | 8/1980 | Isakov et al. | 128/303.1 |
| 4,503,853 | 3/1985 | Ota et al. | 128/303.1 |
| 4,538,609 | 9/1985 | Takenake et al. | 128/303.1 |
| 4,580,557 | 4/1986 | Hertzmann | 128/395 |
| 4,580,559 | 4/1986 | L'Esperance | 128/303.1 |
| 4,597,030 | 6/1986 | Brody et al. | 362/32 |

FOREIGN PATENT DOCUMENTS

| | | | |
|---|---|---|---|
| 0070459 | 1/1983 | European Pat. Off. | 128/303.1 |
| 0075912 | 9/1982 | Japan . | |

*Primary Examiner*—Max Hindenburg
*Attorney, Agent, or Firm*—Alan H. MacPherson; Paul J. Winters; John F. Schipper

[57] ABSTRACT

An insert for guiding and orienting a surgical laser peripheral into a calibration device for calibrating the laser's output is disclosed. This insert is affixable to the output end of the laser peripheral. It is configured as a rigid body of flat sheet stock shaped at its lower end to permit insertion into the aperture of a laser calibration device. It has at its midsection a shoulder which limits insertion into said aperture to a predetermined depth. It has, at its upper end, one or more manually-engagable tabs for manipulating the insert with the peripheral attached. A calibratable laser peripheral which is made up of the peripheral in combination with such a laser calibration insert is also disclosed.

7 Claims, 2 Drawing Sheets

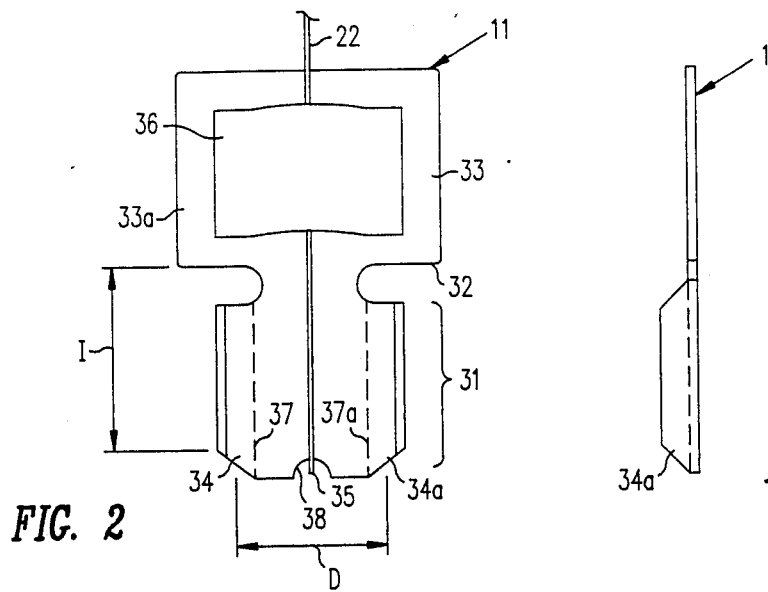
FIG. 2
FIG. 3
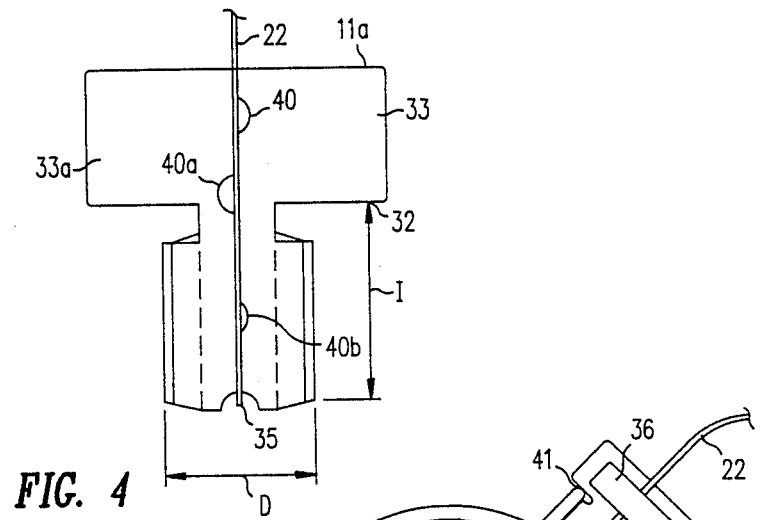
FIG. 4
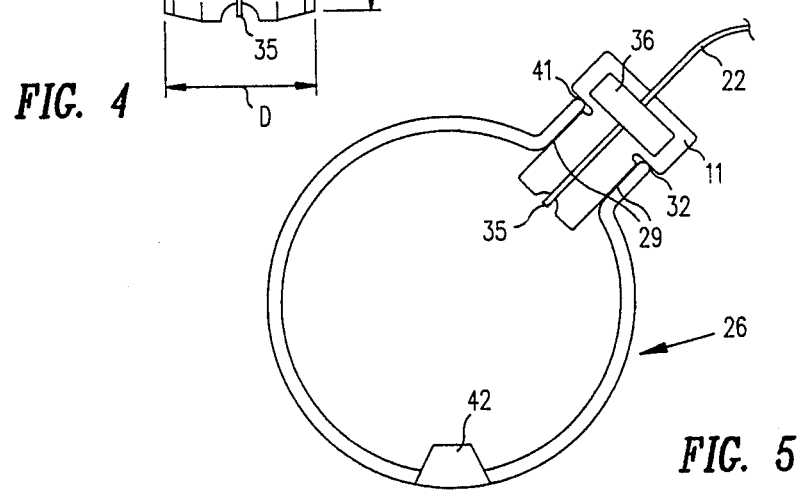
FIG. 5

LASER OUTPUT CALIBRATION TAB

BACKGROUND OF THE INVENTION

1. Field of the Invention

This invention is in the field of medical equipment. More particularly it concerns a fitting for facillitating the calibration of medical lasers to set their outputs to medical or surgical peripheral implements.

2. Description of Prior Art

Surgical techniques employing laser radiation have been in development for several years. Laser beam manipulator implements have been employed as surgical scalpels as illustrated in, for example, U.S. Pat. No. 3,865,113 of Sharon et al; European Patent Application Ser. No. 75,912 (Published Apr. 6, 1983) of Hitachi, Ltd.; and West German Pat. No. 3105297 of Asaki Kogaku Kogyo. Laser implements can also be used to effect blood coagulation or to cauterize as shown by, for example, U.S. Pat. No. 3,487,835 of Koester et al. Laser surgical implements may be macroscale or may be sized for operation under a microscope to perform microsurgery as is described in, for example, U.S. Pat. No. 4,091,814 of Togo. As emphasized in commonly assigned U.S. Pat. No. 4,580,557, these various techniques have created a need for medical laser systems having varied power levels and peripheral attachments, so that a single laser may be used in performing these various techniques.

It is necessary to precisely measure and control the amount of laser radiation delivered to biological tissues in photo-surgical procedures. The appropriate amount of radiation is known to vary with the technique employed. Systems have been developed to control the intensity and duration of the laser radiation energy applied to the treated tissues. See U.S. Pat. Nos. 4,215,694 of Isakov et al; 4,122,853 of Smith; as well as commonly assigned U.S. Pat. No. 4,580,557 and EPO Patent Application No. 75,912. Systems such as the Smith system rely on exposure control devices such as shutters and laser power level control circuits.

The need to control the amount of laser radiation delivered to tissues is aggravated when various peripheral implements, having varying optical properties and power requirements, are used in the same system. In such settings it is advisable to calibrate the laser output actually delivered to the peripheral or by the peripheral immediately before using the peripheral implement so as to assure the desired levels. This calibration must be carried out in a manner which does not compromise the sterilty of the peripheral and which does not subject the peripheral to physical damage as that could change the peripheral's output.

U.S. Pat. No. 4,580,557, which is incorporated herein by reference, shows a laser system in which such calibration of the laser output is carried out by inserting the laser peripheral into a calibration device or senser in which its output can be measured. Such a device is constructed to be relatively insensitive to the exact position of the peripheral in it but nonetheless it is important that the peripheral be inserted into a relatively uniform position. In addition, it is important that the peripheral be inserted in a manner which preserves its sterility by preventing the peripheral from contacting the calibration device. Since the calibration is often carried out during a surgical procedure it is also desirable if the insertion into the calibration device is quick and simple and not an extremely complex or precise operation.

This invention provides a device which facilitates the calibration of peripheral laser surgical implements by simplifying their proper and sterile insertion into a calibration device.

STATEMENT OF THE INVENTION

It has now been found that the calibration of laser outputs through surgical peripherals can be carried out with improved efficiency by the use of an insert which guides the peripheral into the calibration device in a proper orientation. In one aspect, this invention provides the laser calibration device insert. This insert is affixable to the output end of a laser peripheral and is configured as a rigid body of flat sheet stock shaped at its lower end to permit insertion into the aperture of a laser calibration device, having at its midsection a shoulder which limits insertion into said aperture to a predetermined depth and having at its upper end one or more manually-engagable wings for manipulating the insert with the peripheral attached.

In another aspect this invention provides a calibratable laser peripheral which is made up of the peripheral in combination with the laser calibration insert. The output end of the peripheral is attached to the insert and the insert's shoulder limits insertion of the laser peripheral's output end into said aperture to a predetermined depth and having at its upper end one or more manually engagable wings for manipulating the insert with the peripheral attached.

DETAILED DESCRIPTION OF THE INVENTION

Brief description of the Drawings

In this specification, reference will be made to the drawings in which:

FIG. 2 is an about full scale front view of an insert of the invention;

FIG. 3 is a side view of an insert of the invention;

FIG. 4 is a front view of an insert of the invention; and

FIG. 5 is a cross sectional view of a laser peripheral guided into position in a calibration device by means of the insert of this invention.

DESCRIPTION OF PREFERRED EMBODIMENTS

Figure 1:
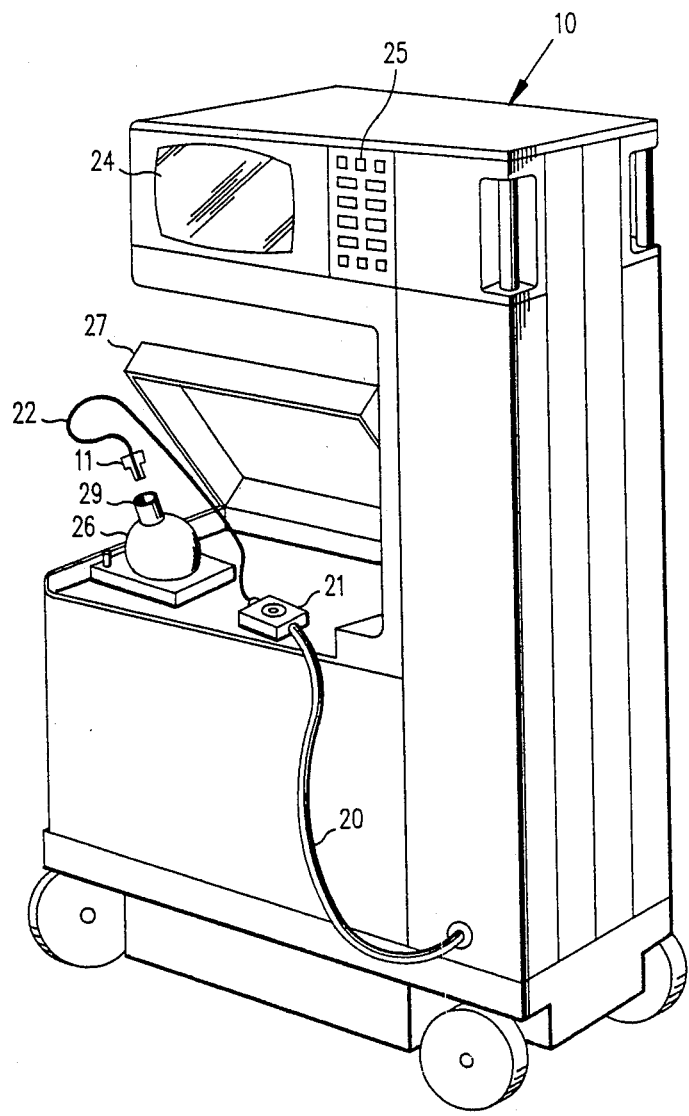
FIG. 1 is a pictorial view of a medical laser system console which is provided to illustrate the context in which the present invention can be used.

Turning to FIG. 1, a medical laser system is illustrated including a laser console 10, a laser output line 20, an optical/electrical coupler 21 and an exemplary peripheral surgical implement 22. The laser console 10 may include an optical system consisting of a laser, directing and attenuating devices, and control electronics which are not shown. A typical laser system is described in U.S. Pat. No. 4,580,557 which has been incorporated herein by reference. The console may include a video display 24 and input key pad 25 by which the operation of the system may be manually monitored and controlled, for example, by reading on display 24 the identity of the attached peripheral implement and by entering via pad 25 power output set points suitable for the particular surgical technique and peripheral implements in use. The laser console also includes other associated elements such as a calibration device 26 stored under a lid 27. Device 26 contains an aperture 29 into which the output end of implement 22 is inserted for calibration. The output end of implement 22 is attached to calibration insert 11 which is adapted to fit into aperture 29 for calibration purposes. It should be understood that the particular peripheral surgical implement shown in FIG. 1 is merely representative. Such implements may also include dermal handpieces, microsurgical scalpels, microsurgical handpieces, intraocular probes, rhinal probes, microcautery probes, macrocautery probes, endoscopic probes, laser microscopic device, and other laser-powered medical implements known in the prior art. They may also include cautery probes and scalpels having tip portions heated by laser radiation, wherein the laser light does not impinge on the tissues.

In FIGS. 2 and 3, a representative calibration insert of the invention 11 is shown to include a lower portion 31 which is sized (dimension D) to fit into aperture 29, a shoulder 32 in its midsection which is positioned to abut the edge of aperture 29 and allow insert 11, as thus the output end of the laser peripheral which is attached to it to go into aperture 29 to a preset insertion depth show in FIG. 2 a dimension I; and an upper region which provides grasping surfaces 33 and 33a. The user can use these surfaces 33 and 33a to manipulate the insert into and out of the calibration aperture. Insert 11 may optionally contain one or more wings or tabs 34 and 34a angled from the portion of the insert that fits into aperture 29. These tabs can have the effect of deforming and giving a tighter engagement with the walls of aperture 29 and thus hold the insert in the aperture without operator assistance. They can also serve to protect the end 35 of laser peripheral 22 which is removably affixed to the insert such as by tape 36. In addition, the lower portion of insert 11 can protect the end 35. Optionally, the lower portion has a cut away 38 which exposes the end 35 of the laser peripheral while affording it protection.

Typically, insert 11 is made from a single piece of flat sheet stock with optional wings 34 and 34a being bent up along lines 37 and 37a respectively. These wings can also protect the laser peripheral from damage or contamination.

Typically, the calibration insert 11 is fabricated from a flat board stock, typically plastic, cardboard, heavy paper or the like. The exact material is unimportant, as long as the stock has sufficient rigidity to form the desired shape and to position the peripheral properly in the calibration aperture. Typical materials are 0.05 inch to 0.10 inch thick paper board stock and 0.02 to 0.06 inch thick polyethylene, polypropylene, polystyrene or a like plastic.

In selecting the materials of construction, it should be borne in mind that the laser peripherals with which the present invention is used are sterilized before use. This sterilization may be carried out by exposure to ethylene oxide or a like sterilizing gas, exposure to sterilizing radiation, or autoclaving in the presence or absence of steam. The materials employed should be able to withstand this sterilization as it is generally carried out after the insert is attached to the peripheral. Similarly, the method of affixing the peripheral to the insert, for example adhesive tape 36 in FIG. 1 should be of polyethylene or the like which can undergo sterilization and permit the sterilizing medium to pass through and sterilize its undersurfaces.

Turning to FIG. 4, a variation 11a of the insert of this invention is shown. Insert 11a has somewhat different proportions than insert 11 but does present a lower portion having a width D which permits insertion into the calibration device aperture 29. In the case of insert 11a, dimension D is achieved with mimimal distortion or bending of the insert as opposed to insert 11 which was sized to give a tighter fit. Insert 11a also has shoulder 32 which permits but limits the insertion into the aperture to a depth I. Peripheral 22 is held into position on the insert by means of gripper tabs 40, 40a and 40b which temporarily clamp the peripheral into position on the insert. Other alternative methods for temporarily attaching the peripheral to the insert can be used, as well.

Turning to FIG. 5, the use of the insert of the present invention is shown. Peripheral 22 is attached to insert 11 by tape 36. Insert 11 is inserted in aperture 29 in device 26 to a predetermined depth I set by shoulder 32 contacting the lip 41 of aperture 29. This places the output end of peripheral 22 in proper position within the calibration device such that when laser light is outputted into the calibration device via output end 35, detector 42 can determine it and provide a proper signal to calibrate. After calibration, the insert is removed from the aperture and the peripheral and the insert are separated.

One advantage of this invention is that it prevents contact between the laser peripheral and the calibration device. The peripheral is sterile and usually the calibration device is not. The insert which contacts the calibration device becomes nonsterile but it is separated and discarded immediately after the calibration event is completed so as to not possibly contaminate the surgical field.

While the present invention has been described with reference to the foregoing preferred embodiments, it will be appreciated by those skilled in the art that the invention can be modified without departing from the spirit of the invention as defined by the following claims.

What is claimed is:

1. A laser calibration device insert removably affixable to the output end of a laser surgery peripheral implement, said insert comprising a rigid body of flat sheet stock shaped into a wider upper region and joined continuously therewith through a transition to a narrower lower region having a bottom edge and two sides, the lower region being sized to permit insertion into the aperture of a laser calibration device and having one or both of its two sides angled from the plane of the flat sheet stock so as to form angled wings to frictionally engage the inner walls of the aperture upon insertion, and the upper region having one or more manually-engageable tabs for manipulating the insert and the transition between the upper and lower regions defining a shoulder which limits insertion of the insert into the aperture to a predetermined depth.

2. The laser calibration device insert of claim 1 wherein the lower region additionally comprises on its bottom surface a notch to expose the output end of a laser surgery peripheral implement affixed to the insert.

3. The laser calibration device insert of claim 1 additionally comprising means for affixing the laser peripheral so as to permit insertion of the laser surgery peripheral implement output end into the aperture of the calibration device.

4. The laser calibration device insert of claim 3 wherein the means for affixing the laser surgery peripheral implement to the insert comprises adhesive tape.

5. The laser calibration device insert of claim 3 wherein the means for affixing the laser surgery peripheral implement to the insert comprises peripheral-engaging gripper tabs.

6. The laser calibration device insert of claim 1 wherein the sheet stock comprises plastic sheet.

7. The laser calibration device insert of claim 1 wherein the sheet stock comprises paper board.

* * * * *